United States Patent

Krahnke et al.

[11] Patent Number: 6,013,753
[45] Date of Patent: Jan. 11, 2000

[54] ORGANOSILICON ENDCAPPER HAVING ONE ALIPHATIC UNSATURATION

[75] Inventors: Robert Harold Krahnke, Midland; Timothy B. Lueder, Mt. Pleasant; Richard Alan Palmer; Nick Evan Shephard, both of Midland, all of Mich.

[73] Assignee: Dow Corning Corporation, Midland, Mich.

[21] Appl. No.: 09/218,365

[22] Filed: Dec. 21, 1998

[51] Int. Cl.[7] .................................................. C08G 77/20
[52] U.S. Cl. ............................. 528/32; 528/35; 556/434; 556/435
[58] Field of Search .................................. 556/434, 435; 528/32, 35

[56] References Cited

U.S. PATENT DOCUMENTS

| | | | |
|---|---|---|---|
| 3,109,013 | 10/1963 | Haluska | 260/448.2 |
| 3,122,522 | 2/1964 | Brown et al. | 260/46.5 |
| 3,151,099 | 9/1964 | Frederic et al. | 260/46.5 |
| 3,161,614 | 12/1964 | Brown et al. | 260/46.5 |
| 3,175,993 | 3/1965 | Weyenberg | 260/45.6 |
| 3,294,739 | 12/1966 | Weyenberg | 260/46.5 |
| 3,334,065 | 8/1967 | Weyenberg | 260/46.5 |
| 3,631,193 | 12/1971 | Young | 260/448.2 |
| 3,671,483 | 6/1972 | Young | 260/32.8 |
| 3,714,109 | 1/1973 | Matherly | 260/32.8 |
| 3,794,556 | 2/1974 | Young | 161/206 |
| 3,819,674 | 6/1974 | Rudolph et al. | 260/448.2 |
| 4,283,519 | 8/1981 | Pines et al. | 529/26 |
| 4,461,867 | 7/1984 | Surprenant | 524/788 |
| 4,525,400 | 6/1985 | Surprenant | 428/54 |
| 4,525,566 | 6/1985 | Homan et al. | 528/17 |
| 4,579,964 | 4/1986 | Totten et al. | 556/434 |
| 4,599,394 | 7/1986 | Lucas | 528/15 |
| 4,616,076 | 10/1986 | Ona et al. | 528/15 |
| 4,652,624 | 3/1987 | Allen et al. | 528/17 |
| 4,731,411 | 3/1988 | Lucas | 524/860 |
| 4,743,474 | 5/1988 | Homan | 427/387 |
| 4,772,675 | 9/1988 | Klosowski et al. | 528/15 |
| 4,849,491 | 7/1989 | Ogawa et al. | 528/15 |
| 4,871,827 | 10/1989 | Klosowski et al. | 528/17 |
| 4,888,404 | 12/1989 | Klowowski et al. | 528/15 |
| 4,898,910 | 2/1990 | Kamis et al. | 524/860 |
| 4,956,435 | 9/1990 | Chu et al. | 528/17 |
| 5,017,672 | 5/1991 | Krahnke et al. | 528/23 |
| 5,079,311 | 1/1992 | Colas | 525/478 |
| 5,091,484 | 2/1992 | Colas et al. | 525/477 |
| 5,097,054 | 3/1992 | Yamamoto et al. | 556/451 |
| 5,175,328 | 12/1992 | Okawa et al. | 556/451 |
| 5,194,649 | 3/1993 | Okawa | 556/451 |
| 5,272,243 | 12/1993 | Nakashima et al. | 528/31 |
| 5,286,766 | 2/1994 | Arai et al. | 523/213 |
| 5,359,109 | 10/1994 | Ritscher et al. | 556/434 |
| 5,378,790 | 1/1995 | Michalczyk et al. | 528/35 |
| 5,403,881 | 4/1995 | Okawa et al. | 524/261 |
| 5,416,230 | 5/1995 | Jung et al. | 556/451 |
| 5,442,083 | 8/1995 | Kobayashi | 556/434 |
| 5,446,185 | 8/1995 | Cobb et al. | 556/451 |
| 5,548,051 | 8/1996 | Michalczyk et al. | 528/15 |
| 5,557,000 | 9/1996 | Minemura | 556/434 |
| 5,567,764 | 10/1996 | Brasseur et al. | 524/755 |
| 5,567,833 | 10/1996 | Iwahara et al. | 556/434 |
| 5,581,008 | 12/1996 | Kobayashi | 556/434 |
| 5,639,845 | 6/1997 | Inomata et al. | 528/15 |
| 5,670,686 | 9/1997 | Cobb et al. | 556/445 |
| 5,733,996 | 3/1998 | De Buyl et al. | 528/17 |
| 5,840,794 | 11/1998 | Palmer | 524/425 |

FOREIGN PATENT DOCUMENTS 0 803 541 A1 10/1997 European Pat. Off. ........ C08L 83/04

Primary Examiner—Margaret G. Moore
Attorney, Agent, or Firm—Patricia M. Scaduto

[57] ABSTRACT

An organosilicon compound comprising one aliphatic unsaturation described by formula

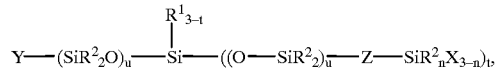

where each $R^1$ is an independently selected hydrocarbon radical free from aliphatic unsaturation comprising 1 to about 18 carbon atoms; each $R^2$ is an independently selected hydrocarbon radical free from aliphatic unsaturation comprising 1 to about 18 carbon atoms; each X is independently selected from the group consisting of halogen, alkoxy, acyloxy, and ketoximo; t is 2 or 3; n is 0, 1, or 2; u is 0 or 1; each Z is independently selected from the group consisting of divalent hydrocarbon radicals free of aliphatic unsaturation comprising about 2 to 18 carbon atoms and a combination of divalent hydrocarbon radicals and siloxane segments; and Y is selected from the group consisting of hydrocarbon radicals comprising one aliphatic unsaturation and 2 to about 18 carbon atoms and a combination of hydrocarbon radicals, siloxane segments, and a divalent hydrocarbon radical free of aliphatic unsaturation comprising about 2 to 18 carbon atoms. The organosilicon compounds comprising one aliphatic unsaturation of the present invention are useful as endcappers for polymers.

20 Claims, No Drawings

ORGANOSILICON ENDCAPPER HAVING ONE ALIPHATIC UNSATURATION

FIELD OF THE INVENTION

An organosilicon compound comprising one aliphatic unsaturation described by formula

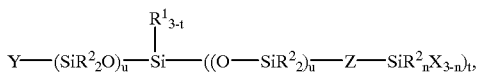

where each $R^1$ is an independently selected hydrocarbon radical free from aliphatic unsaturation comprising 1 to about 18 carbon atoms; each $R^2$ is an independently selected hydrocarbon radical free from aliphatic unsaturation comprising 1 to about 18 carbon atoms; each X is independently selected from the group consisting of halogen, alkoxy, acyloxy, and ketoximo; t is 2 or 3; n is 0, 1, or 2; u is 0 or 1; each Z is independently selected from the group consisting of divalent hydrocarbon radicals free of aliphatic unsaturation comprising about 2 to 18 carbon atoms and a combination of divalent hydrocarbon radicals and siloxane segments; and Y is selected from the group consisting of hydrocarbon radicals comprising one aliphatic unsaturation and 2 to about 18 carbon atoms and a combination comprising one aliphatic unsaturation of hydrocarbon radicals, siloxane segments, and a divalent hydrocarbon radical free of aliphatic unsaturation comprising about 2 to 18 carbon atoms.

BACKGROUND OF THE INVENTION

Polyorganosiloxane compositions which cure to elastomeric materials at room temperature are well known. Such compositions can be obtained by mixing polydiorganosiloxanes having reactive or hydrolyzable groups, such as silanol or alkoxy groups, with silane crosslinking agents, for example, alkoxysilanes, acetoxysilanes, oximosilanes, or aminosilanes, and catalysts as needed. Generally, the polydiorganosiloxanes may have 1 to 3 reactive groups per chain end. Compositions comprising these ingredients can then be cured by exposure to atmospheric moisture at room temperature.

The cure rate of a particular composition is dependent on a number of factors including the type of reactive or hydrolyzable group utilized. It is known that different hydrolyzable groups have different reactivities and even the same type of hydrolyzable group can have different reactivities. For example, in the presence of moisture, a silicon-bonded acetoxy group will hydrolyze more rapidly than a silicon-bonded alkoxy group. In addition if, for example, a silicon-bonded trialkoxy group is present on a polymer, it is believed that each silicon-bonded alkoxy group has a different reactivity, with the alkoxy group first reacted being "most reactive." Generally, once the first alkoxy group on a silicon atom reacts it takes a longer time for the second alkoxy group on the same silicon atom to react, and even longer for the third. Therefore, it would be desirable to prepare an organosilicon compound which can endcap a polymer and be capable of providing more than one "most" reactive hydrolyzable group per polymer chain end.

The objective of the present invention is to prepare an organosilicon compound comprising one aliphatic unsaturation which is capable of endcapping a polymer and providing more than one "most" reactive hydrolyzable group per polymer chain end.

SUMMARY OF THE INVENTION

The present invention is an organosilicon compound comprising one aliphatic unsaturation described by formula

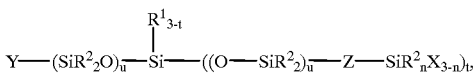

where each $R^1$ is an independently selected hydrocarbon radical free from aliphatic unsaturation comprising 1 to about 18 carbon atoms; each $R^2$ is an independently selected hydrocarbon radical free from aliphatic unsaturation comprising 1 to about 18 carbon atoms; each X is independently selected from the group consisting of halogen, alkoxy, acyloxy, and ketoximo; t is 2 or 3; n is 0, 1, or 2; u is 0 or 1; each Z is independently selected from the group consisting of divalent hydrocarbon radicals free of aliphatic unsaturation comprising about 2 to 18 carbon atoms and a combination of divalent hydrocarbon radicals and siloxane segments; and Y is selected from the group consisting of hydrocarbon radicals comprising one aliphatic unsaturation and 2 to about 18 carbon atoms and a combination comprising one aliphatic unsaturation of hydrocarbon radicals, siloxane segments, and a divalent hydrocarbon radical free of aliphatic unsaturation comprising about 2 to about 18 carbon atoms.

DETAILED DESCRIPTION OF THE INVENTION

The present invention is an organosilicon compound comprising one aliphatic unsaturation described by formula (I)

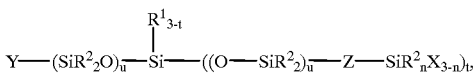

where each $R^1$ is an independently selected hydrocarbon radical free from aliphatic unsaturation comprising 1 to about 18 carbon atoms; each $R^2$ is an independently selected hydrocarbon radical free from aliphatic unsaturation comprising 1 to about 18 carbon atoms; each X is independently selected from the group consisting of halogen, alkoxy, acyloxy, and ketoximo; t is 2 or 3; n is 0, 1, or 2; u is 0 or 1; each Z is independently selected from the group consisting of divalent hydrocarbon radicals free of aliphatic unsaturation comprising about 2 to 18 carbon atoms and a combination of divalent hydrocarbon radicals and siloxane segments described by formula

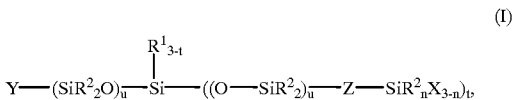

where $R^2$ is as defined above; each G is an independently selected divalent hydrocarbon radical free of aliphatic unsaturation comprising about 2 to 18 carbon atoms; and c is a whole number from 1 to about 6; and Y is selected from the group consisting of hydrocarbon radicals comprising one aliphatic unsaturation and 2 to about 18 carbon atoms and a combination comprising one aliphatic unsaturation of hydrocarbon radicals, siloxane segments, and a divalent hydrocarbon radical free of aliphatic unsaturation comprising about 2 to about 18 carbon atoms described by formula

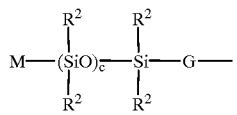

where $R^2$, G, and c are as defined above and M is an independently selected hydrocarbon radical comprising one aliphatic unsaturation and about 2 to about 18 carbon atoms.

In formula (I), each $R^1$ is an independently selected hydrocarbon radical free from aliphatic unsaturation comprising 1 to about 18 carbon atoms. The hydrocarbon radicals free from aliphatic unsaturation represented by $R^1$ may be substituted or unsubstituted. Examples of hydrocarbon radicals free from aliphatic unsaturation include alkyl radicals, aryl radicals, and aralkyl radicals. Examples of alkyl radicals include methyl, ethyl, hexyl, octadecyl, cyclobutyl, cyclopentyl, cyclohexyl, 3,3,3-trifluoropropyl, chloromethyl, and chlorocyclopentyl. Examples of aryl radicals include phenyl, tolyl, xylyl, 2,4-dichlorophenyl, and tetrachlorophenyl. Examples of aralkyl radicals include benzyl, beta-phenylethyl, gamma-tolylpropyl, para-chlorobenzyl, and 2-(bromophenyl)propyl. Preferably, each $R^1$ is selected from the group consisting of alkyl radicals comprising 1 to about 8 carbon atoms and aryl radicals comprising about 6 to 8 carbon atoms. More preferably, $R^1$ is an alkyl radical comprising 1 to about 8 carbon atoms. Most preferably each $R^1$ is methyl.

In formula (I), each $R^2$ is an independently selected hydrocarbon radical free from aliphatic unsaturation comprising 1 to about 18 carbon atoms. The hydrocarbon radicals free from aliphatic unsaturation represented by $R^2$ may be substituted or unsubstituted. Examples of hydrocarbon radicals free from aliphatic unsaturation include alkyl radicals, aryl radicals, and aralkyl radicals. Examples of $R^2$ are as described above for $R^1$. Preferably each $R^2$ is an independently selected alkyl radical. More preferably each $R^2$ is an independently selected alkyl radical comprising 1 to about 8 carbon atoms.

In formula (I), each X is independently selected from the group consisting of halogen, alkoxy, acyloxy, and ketoximo. The halogen atoms can be chlorine, bromine, fluorine, and iodine. Examples of alkoxy groups include methoxy, ethoxy, iso-propoxy, butoxy, cyclohexoxy, phenoxy, 2-chloroethoxy, 3,3,3-trifluoropropoxy, 2-methoxyethoxy, and p-methoxyphenoxy. Examples of acyloxy groups include acetoxy, propionoxy, benzoyloxy, and cyclohexoyloxy. Examples of ketoximo groups include dimethylketoximo, methylethylketoximo, methylpropylketoximo, methylbutylketoximo, and diethylketoximo. Preferably each X is independently selected from the group consisting of alkoxy, acyloxy, and ketoximo. More preferably each X is independently selected from the group consisting of alkoxy and acyloxy, with each X being an independently selected alkoxy group being most preferred.

In formula (I), subscript t is 2 or 3 and is preferably 2; subscript n is 0, 1, or 2 and is preferably 0 or 1; and subscript u is 0 or 1.

In formula (I), each Z is independently selected from the group consisting of divalent hydrocarbon radicals free of aliphatic unsaturation comprising about 2 to 18 carbon atoms and a combination of divalent hydrocarbon radicals and siloxane segments described by formula

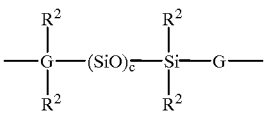

where $R^2$ is as defined above; each G is an independently selected divalent hydrocarbon radical free of aliphatic unsaturation comprising about 2 to 18 carbon atoms; and c is a whole number from 1 to about 6.

Examples of the divalent hydrocarbon radicals free of aliphatic unsaturation represented by Z and G include alkylene radicals, arylene radicals and aralkylene radicals. The divalent hydrocarbon radicals represented by Z and G may be substituted or unsubstituted. Examples of alkylene radicals include ethylene, methylmethylene, propylene, butylene, pentylene, hexylene, cyclopentylene, cyclohexylene, chloroethylene, and chlorocyclopentylene. Examples of arylene radicals include phenylene, tolylene, xylylene, 2,4-dichlorophenylene, and tetrachlorophenylene. Examples of aralkylene radicals include benzylene, beta-phenylethylene, gamma-tolylpropylene, para-chlorobenzylene, and 2(bromophenyl)propylene. When Z is a combination of divalent hydrocarbon radicals and siloxane segments as described above, each G is preferably an independently selected alkylene radical, and each G is more preferably an independently selected alkylene radical comprising about 2 to 8 carbon atoms. Preferably, each Z is an independently selected divalent hydrocarbon radical free from aliphatic unsaturation. It is more preferred for each Z to be an independently selected alkylene radical, with an independently selected alkylene radical comprising about 2 to 8 carbon atoms being most preferred for Z.

In formula (I), Y is selected from the group consisting of hydrocarbon radicals comprising one aliphatic unsaturation and about 2 to 18 carbon atoms and a combination comprising one aliphatic unsaturation of hydrocarbon radicals, siloxane segments, and a divalent hydrocarbon radical free of aliphatic unsaturation comprising about 2 to about 18 carbon atoms described by formula

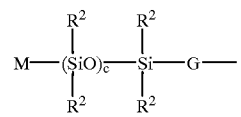

where $R^2$, G, and c are as defined above and M is a hydrocarbon radical comprising one aliphatic unsaturation and 2 to about 18 carbon atoms.

The hydrocarbon radicals of Y and M may be substituted or unsubstituted. Examples of the hydrocarbon radicals comprising one aliphatic unsaturation represented by Y and M include alkenyl radicals such as vinyl, allyl, butenyl, hexenyl, and octenyl, and cycloalkenyl radicals such as cyclopentenyl, cyclohexenyl, and chlorocyclopentenyl. With non-cyclic compounds comprising one aliphatic unsaturation, it is preferred for the aliphatic unsaturation to be at the terminal end of the hydrocarbon radical attached to silicon, for example as in 1-butenyl, i.e. $H_2C=CHCH_2CH_2-$.

When Y is a combination comprising one aliphatic unsaturation of hydrocarbon radicals, siloxane segments, and a divalent hydrocarbon radical free of aliphatic unsaturation as described above, it is preferred that G be an alkylene radical and M an alkenyl radical, and more preferable that G be an alkylene radical comprising about 2 to 8 carbon atoms and M an alkenyl radical comprising 2 to about 8 carbon atoms. Preferably, Y is a hydrocarbon radical comprising one aliphatic unsaturation. It is more preferred for Y to be an alkenyl radical, with an alkenyl radical comprising 2 to about 8 carbon atoms being most preferred for Y.

The organosilicon compound comprising one aliphatic unsaturation described by formula (I) may be prepared by mixing an organosiloxane comprising aliphatic unsaturations described by formula

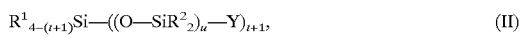  (II)

with a silicon-bonded hydrogen compound described by formula

  (III)

in the presence of a hydrosilylation catalyst, where $R^1$, $R^2$, X, Y, t, u, and n are as defined above.

Both the organosiloxane comprising aliphatic unsaturations described by formula (II) and the silicon-bonded hydrogen compound described by formula (III) may be prepared by known methods and are commercially available.

Catalysts typically employed for hydrosilylation reactions, such as platinum group metal-containing catalysts are used as catalysts for the reaction between the organosiloxane comprising aliphatic unsaturations described by formula (II) and the silicon-bonded hydrogen compound described by formula (III). By "platinum group metal" it is meant ruthenium, rhodium, palladium, osmium, iridium, and platinum. Platinum group metal-containing catalysts particularly useful in the present composition are the platinum complexes prepared as described by Willing, U.S. Pat. No. 3,419,593, and Brown et al, U.S. Pat. No. 5,175,325, each of which is hereby incorporated by reference to show such complexes and their preparation. Preferred catalysts are complexes of platinum with vinylsiloxane. Other examples of useful platinum group metal-containing catalysts can be found in Lee et al., U.S. Pat. No. 3,989,668; Chang et al., U.S. Pat. No. 5,036,117; Ashby, U.S. Pat. No. 3,159,601; Lamoreaux U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalysts and methods for their preparation.

The amount of catalyst useful in effecting the hydrosilylation reaction to make the composition of the present invention is not narrowly limited as long as there is a sufficient amount present to accelerate a reaction between the hydrosilyl groups and the aliphatic unsaturated groups. The appropriate amount of the catalyst will depend upon the particular catalyst used. In general as low as about 0.1 part by weight of platinum group metal based on 1 million parts by weight of total reactants may be useful (ie. 0.1 ppm). Preferably the amount of platinum group metal is from about 1 to 60 ppm. More preferred is from about 10 to 40 ppm platinum group metal.

The platinum group metal-containing catalyst may be added as a single species or as a mixture of two or more different species. Adding the catalyst as a single species is preferred.

The temperature of the hydrosilylation reaction is not strictly specified, but usually falls within the range of about 20° to 150° C. and preferably within the range of about 30° to 120° C.

The molar ratio of aliphatic unsaturated groups to hydrosilyl groups useful in the present invention will vary depending upon the individual compositions. However, to ensure the highest yield of the organosilicon compound comprising one aliphatic unsaturation, the molar ratio of aliphatic unsaturated groups to hydrosilyl groups should be approximately t+1/t:1, where t is as defined above.

After completion of the hydrosilylation reaction, the organosilicon compound comprising one aliphatic unsaturation described by formula (I) may be recovered by standard methods for separating liquid mixtures, such as distillation from the reaction mixture under reduced pressure, recrystallization, or solvent fractionation.

The organosilicon compounds comprising one aliphatic unsaturation of the present invention are useful for endcapping polymers and as adhesion promoters and crosslinkers. Polymers endcapped with the organosilicon compounds of the present invention can be used for preparing sealants, adhesives, and coatings. Persons skilled in the art will also understand that the organosilicon compounds of the present invention in addition to endcapping polymers may also be found pendant on the polymer chain.

This invention is further illustrated by the following example which is presented for that purpose and is not intended to limit the scope of the claims herein. As used in the example, Me is methyl, Et is ethyl, and Vi is vinyl.

EXAMPLE 20.44 g (0.15 mol) tetravinylsilane and 5000 ppm of a solution of a platinum vinylsiloxane complex containing 30 ppm platinum metal were heated to 100° C. The heat was then removed and 60.41 g (0.45 mol) of methyldiethoxysilane were added dropwise over a period of about 45 min. with sufficient stirring to maintain a pot temperature of approximately 100–115° C. Analysis of the reaction mixture by gas liquid chromatography (Hewlett Packard 5890 Series II) showed a yield of approximately 49% of an organosilicon compound comprising one aliphatic unsaturation. 14 g of the reaction mixture containing about a 70% pure sample of the organosilicon compound having the following formula was isolated by distilling at 175° C. under 2 mm Hg pressure.

We claim:

1. An organosilicon compound comprising one aliphatic unsaturation described by formula

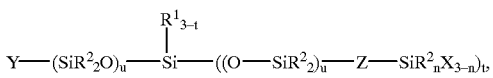

where each $R^1$ is an independently selected hydrocarbon radical free from aliphatic unsaturation comprising 1 to about 18 carbon atoms; each $R^2$ is an independently selected hydrocarbon radical free from aliphatic unsaturation comprising 1 to about 18 carbon atoms; each X is independently selected from the group consisting of halogen, alkoxy, acyloxy, and ketoximo; t is 2 or 3; n is 0, 1, or 2; u is 0 or 1; each Z is independently selected from the group consisting of divalent hydrocarbon radicals free of aliphatic unsaturation comprising about 2 to 18 carbon atoms and a combination of divalent hydrocarbon radicals and siloxane segments described by formula

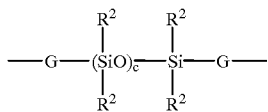

where $R^2$ is as defined above; each G is an independently selected divalent hydrocarbon radical free of aliphatic unsaturation comprising about 2 to 18 carbon atoms; and c is a whole number from 1 to about 6; and Y is selected from the group consisting of hydrocarbon radicals comprising one aliphatic unsaturation and 2 to about 18 carbon atoms and a combination comprising one aliphatic unsaturation of hydrocarbon radicals, siloxane segments, and a divalent hydrocarbon radical free of aliphatic unsaturation comprising about 2 to 18 carbon atoms described by formula

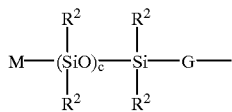

where $R^2$, G, and c are as defined above and M is a hydrocarbon radical comprising one aliphatic unsaturation and 2 to about 18 carbon atoms.

2. The organosilicon compound of claim 1, where each Z is independently selected from the group consisting of divalent hydrocarbon radicals free of aliphatic unsaturation comprising about 2 to 18 carbon atoms and a combination of divalent hydrocarbon radicals and siloxane segments described by formula

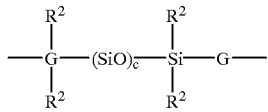

where $R^2$ is as defined above; each G is an independently selected alkylene; and c is a whole number from 1 to about 6.

3. The organosilicon compound of claim 1, where each Z is an independently selected divalent hydrocarbon radical free of aliphatic unsaturation and Y is a hydrocarbon radical comprising one aliphatic unsaturation.

4. The organosilicon compound of claim 1, where each Z is an independently selected alkylene radical and Y is an alkenyl radical.

5. The organosilicon compound of claim 1, where each Z is an independently selected alkylene radical comprising about 2 to 8 carbon atoms and Y is an alkenyl radical comprising 2 to about 8 carbon atoms.

6. The organosilicon compound of claim 1, where each X is independently selected from the group consisting of alkoxy, acyloxy, and ketoximo.

7. The organosilicon compound of claim 3, where each X is independently selected from the group consisting of alkoxy, acyloxy, and ketoximo.

8. The organosilicon compound of claim 1, where each X is independently selected from the group consisting of alkoxy and acyloxy.

9. The organosilicon compound of claim 3, where each X is independently selected from the group consisting of alkoxy and acyloxy.

10. The organosilicon compound of claim 1, where each X is an independently selected alkoxy group.

11. The organosilicon compound of claim 3, where each X is an independently selected alkoxy group.

12. The organosilicon compound of claim 5, where each X is an independently selected alkoxy group.

13. The organosilicon compound of claim 3, where t is 3.

14. The organosilicon compound of claim 7, where t is 3.

15. The organosilicon compound of claim 9, where t is 3.

16. The organosilicon compound of claim 12, where t is 3.

17. The organosilicon compound of claim 3, where n is 0 or 1.

18. The organosilicon compound of claim 7, where n is 0 or 1.

19. The organosilicon compound of claim 11, where n is 0 or 1.

20. The organosilicon compound of claim 16, where n is 0 and each $R^2$ is an independently selected alkyl radical comprising 1 to about 8 carbon atoms.

* * * * *